United States Patent [19]
Dietrich

[11] Patent Number: 4,783,794
[45] Date of Patent: Nov. 8, 1988

[54] BAGGAGE INSPECTION SYSTEM

[75] Inventor: Rolf Dietrich, Hofheim, Fed. Rep. of Germany

[73] Assignee: Heimann GmbH, Fed. Rep. of Germany

[21] Appl. No.: 886,362

[22] Filed: Jul. 17, 1986

[30] Foreign Application Priority Data

Aug. 29, 1985 [DE] Fed. Rep. of Germany ....... 3530955

[51] Int. Cl.⁴ .......................................... G01N 23/04
[52] U.S. Cl. ....................................... 378/57; 378/62;
378/208; 250/328; 198/817
[58] Field of Search .................. 378/51, 57, 62, 58,
378/208; 250/328; 198/817

[56] References Cited

U.S. PATENT DOCUMENTS

| | | | |
|---|---|---|---|
| 1,405,233 | 1/1922 | Lemoine | 198/817 |
| 2,169,483 | 8/1939 | Adrian | 378/57 |
| 2,813,617 | 11/1957 | Sheetz | 198/817 |
| 3,356,205 | 12/1967 | McLeod | 198/817 |
| 3,808,444 | 4/1974 | Schneeberger | 378/57 |
| 3,881,605 | 5/1975 | Grossman | 198/394 |
| 3,986,604 | 10/1976 | Siryz | 198/395 |
| 3,997,065 | 12/1976 | Jaksch | 198/394 |
| 4,430,568 | 2/1984 | Yoshida et al. | 378/57 |
| 4,599,740 | 7/1986 | Cable | 378/57 |

FOREIGN PATENT DOCUMENTS

| | | |
|---|---|---|
| 2532248 | 11/1976 | Fed. Rep. of Germany. |
| 2213506 | 2/1974 | France. |
| 2110037 | 8/1983 | United Kingdom. |

OTHER PUBLICATIONS

Principles, History, and Status of Dual-Energy Computerized "Tomographic Explosives Detection," Roder, 8262 Journal of Testing and Evaluation 13, No. 3 (May 1985).

*Primary Examiner*—Craig E. Church
*Assistant Examiner*—John C. Freeman
*Attorney, Agent, or Firm*—Hill, Van Santen, Steadman & Simpson

[57] ABSTRACT

A baggage inspection system has a conveyor path disposed between an X-ray source, which genertes an X-ray beam, and a radiation detector for detecting radiation passing through articles on the conveyor path. The conveyor path is formed by two surfaces disposed at a right angle relative to each other, with the right angle being inclined relative to the horizontal so that articles on the conveyor path are forced by gravity to lie against one of the surfaces. At least one of the surfaces is a moveable surface, and the other surface may also be a moveable surface, or a roller surface or a plate against which the articles slide. The radiation detector may be an angled detector row so as to encompass substantially all of the radiation beam within its field of view.

3 Claims, 1 Drawing Sheet

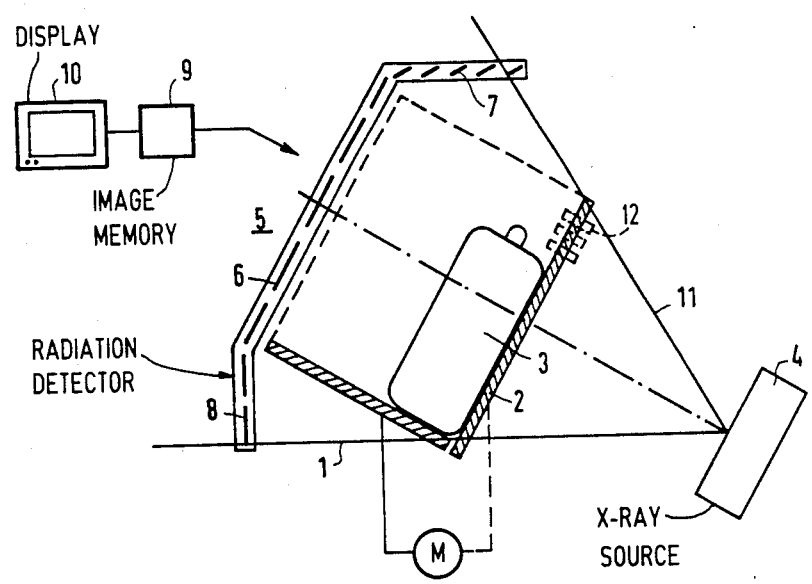

BAGGAGE INSPECTION SYSTEM

BACKGROUND OF THE INVENTION

1. Field of the Invention

The present invention relates to baggage inspection systems, and in particular to such system having a transport path for moving articles to be inspected between an x-ray source generating an x-ray beam and an x-ray detector array.

2. Description of the Prior Art

A baggage inspection system is described in U.S. Pat. No. 3,808,444 having a horizontal conveyor belt for moving articles to be inspected past a radiation source and a radiation detector. In order to achieve a useable inspection result, it is necessary to conduct the articles to be inspected, particularly suitcases, past the radiation source and the radiation detector in an upright position, because the articles usually have a thickness which is less than their height.

As a result of jolting of the conveyor belt as well as upon transfer from one belt to another or to a runway, suitcases which are provided with small feet or wheels frequently fall over. The operating sequence of the system is thereby disrupted, and if such a fall occurs before transillumination of the object by the radiation source, insufficient radiation penetration occurs and thus an unuseable inspection result is obtained.

SUMMARY OF THE INVENTION

It is an object of the present invention to provide a baggage inspection system, wherein articles to be inspected are moved through a radiation beam in which it is not possible for the articles being inspected to tip over, and thus useable inspection results are always obtained.

The above object is achieved in accordance with the principles of the present invention in a baggage inspection system having a conveying path formed by two surfaces disposed at a right angle with respect to each other, with the right angle being inclined relative to the horizontal so that the articles to be inspected lie against both surfaces as a result of their weight. A radiation source is disposed behind one of the surfaces so that the article always presents itself in an upright position with respect to the radiation beam.

One of the two surfaces comprising the conveyor path is a moveable surface, such as a conveyor belt. The other surface may also be a conveyor belt, or may be a roller surface, or may be a stationary slide plate against which the articles slide as they are moved by the moveable surface. If the conveyor path is formed by two conveyor belts, the two belts can be driven by a common motor.

The radiation detector can be formed by an angled row of individual detectors having a central section disposed substantially parallel to one surface of the conveyor path, and having two lateral sections disposed at opposite sides of the central section angled at an obtuse angle relative thereto in a direction toward the conveying path. It is thus possible to cover all normally occurring sizes of articles for inspection with a minimum of individual detectors. Small baggage articles will be disposed closer to the radiation source disposed behind one of the two conveyor surfaces, thereby resulting in the added advantage that such smaller articles will be shown enlarged.

In some arrangements, it is possible that locations may exist, wherein the radiation from the radiation source must penetrate both conveyor surfaces, for example, both conveyor belts. The added thickness of the two conveyor surfaces, particularly of the belts, due to oblique irradiation can be electrically compensated.

DESCRIPTION OF THE DRAWINGS

The single FIGURE shows a schematic end view, partly in section, of a baggage inspection device constructed in accordance with the principles of the present invention.

DESCRIPTION OF THE PREFERRED EMBODIMENTS

A baggage inspection system constructed in accordance with the principles of the present invention is schematically shown in the drawing. The system includes a conveyor path consisting of two conveyor surfaces 1 and 2 which are disposed at a right angle relative to each other. The right angle is unsymmetrically inclined relative to the horizontal meaning the right angle formed by the surfaces 1 and 2 is not bisected by veritcal line perpendicular to the horizontal so that the surfaces 1 and 2 form respective angles with the horizontal of other than 45°. Thus, an article 3 to be inspected such as, for example, a suitcase, will lie against both surfaces 1 and 2 as a result of its weight.

A radiation source 4, such as an X-ray source, is disposed behind one of the conveyor surfaces, such as the conveyor surface 2, and a radiation detector 5 is disposed so that the article 3 passes between the radiation source 4 and the detector 5 and is penetrated by a radiation beam 11 generated by the source 4. Small articles which may be inspected will thus have an enlarged image on the radiation detector 5.

The radiation detector 5 is formed by an angled row of individual detectors and has a central section 6 disposed substantially parallel to the conveyor surfae 2 behind which the radiation source 4 is disposed, and also has two lateral sections 7 and 8 disposed on opposite sides of the central section 6 and angled at an obtuse angle relative to the central section 6 in the direction toward the conveyor surfaces 1 and 2. The individual detectors of the radiation detector 5 are connected to an image memory 9, as schematically by the arrow, in which picture element information is formed in a known manner and stored line-by-line. The plane of the radiation beam 11 is disposed perpendicularly with respect to the direction of transport of the articles 3 through the beam. A shadow image of the article 3 is thereby produced on a display 10.

Only one of the conveyor surfaces 1 and 2 need be a moveable surface such as, for example, a conveyor belt. The other surface may be another moving conveyor belt, a roller surface (as indicated by rollers 12 shown in dashed lines), or a stationary plate which the article 3 slides as it is transported by the moveable surface. If the surfaces 1 and 2 are both moving conveyor belts, the two belts can be synchronously driven by a common motor M.

Although modifications and changes may be suggested by those skilled in the art it is the intention of the inventor to embody within the patent warranted hereon all changes and modifications as reasonably and properly come within the scope of his contribution to the art.

I claim as my invention:

1. A baggage inspection system comprising:

an X-ray source for generating an X-ray beam having a central ray;

a radiation detector disposed for detecting radiation from said X-ray source;

a conveyor path disposed between said X-ray source and said radiation detector for transporting articles through said X-ray beam in a transport direction, said conveyor path consisting of two conveyor surfaces disposed at a right angle with respect to each other, at least one of said conveyor surfaces being movable for transporting said articles, said right angle being unsymmetrically inclined relative to a horizontal direction which is transverse with respect to the transport direction such that said articles lie against both conveyor surfaces as a result of the weight of the articles, and one of said conveyor surfaces being disposed between said X-ray source and said articles at substantially a right angle relative to said central ray; and means for generating a visible image of said articles from signals received from said radiation detector.

2. A baggage inspection system is claimed in claim 1, wherein said radiation detector comprises a central section disposed substantially parallel to said one conveyor surface disposed between said X-ray source and the articles, and two lateral sections disposed on opposite sides of said central section and bent at an obtuse angle relative to said central section in a direction toward said conveyor path.

3. A baggage inspection system as claimed in claim 1, wherein said moveable conveyor surface is formed by a conveyor belt, and the other of said conveyor surfaces is a roller surface.

* * * * *